(12) United States Patent
Huang et al.

(10) Patent No.: US 8,746,088 B2
(45) Date of Patent: Jun. 10, 2014

(54) CYCLE LIFE TESTING MACHINE FOR PIVOTABLE ARTICLES

(75) Inventors: Teng-Tsung Huang, New Taipei (TW); Yong-Bing Hu, Shenzhen (CN); Yuan-Zhao Li, Shenzhen (CN); Zhan Shang, Shenzhen (CN)

(73) Assignees: Hong Fu Jin Precision Industry (ShenZhen) Co., Ltd., Shenzhen (CN); Hong Hai Precision Industry Co., Ltd., New Taipei (TW)

( * ) Notice: Subject to any disclaimer, the term of this patent is extended or adjusted under 35 U.S.C. 154(b) by 225 days.

(21) Appl. No.: 13/303,401

(22) Filed: Nov. 23, 2011

(65) Prior Publication Data

US 2013/0000424 A1    Jan. 3, 2013

(30) Foreign Application Priority Data

Jun. 28, 2011    (CN) .......................... 2011 1 0176814

(51) Int. Cl.
*G01M 99/00*    (2011.01)

(52) U.S. Cl.
USPC .......................................................... 73/865.3

(58) Field of Classification Search
None
See application file for complete search history.

(56) References Cited

U.S. PATENT DOCUMENTS

| | | | | |
|---|---|---|---|---|
| 2,657,573 A | * | 11/1953 | Castricum | 73/794 |
| 5,038,619 A | * | 8/1991 | Hueck | 73/810 |
| 5,567,884 A | * | 10/1996 | Dickinson et al. | 73/814 |
| 2008/0257057 A1 | * | 10/2008 | Habeger et al. | 73/808 |

* cited by examiner

*Primary Examiner* — Robert R Raevis
(74) *Attorney, Agent, or Firm* — Novak Druce Connolly Bove + Quigg LLP

(57) ABSTRACT

A cycle life testing machine includes a controller, a clamping device, a driver, and a cycle device. The cycle device includes a servo motor, an actuator, a shaft, and a swing rod. The controller sends a signal to control the driver to trigger working of the servo motor, and the servo motor drives the actuator and the shaft rotate to swing the swing rod in a cycle procedure specified by the controller.

19 Claims, 6 Drawing Sheets

CYCLE LIFE TESTING MACHINE FOR PIVOTABLE ARTICLES

BACKGROUND

1. Technical Field

The present disclosure relates to a testing machine, and particular to a cycle life testing machine.

2. Description of the Related Art

Pivotable articles such as pivotable carrying cases for carrying and protecting portable electronic device such as mobile phones or tablet personal computers are usually cycle life tested when manufactured. The pivotable article has a first portion that is hinged to a second portion. During cycle life tests, the first portion of the case is secured in a fixed first position, and the second portion of the case is pivoted towards and away from the first portion along the hinge connecting the first and second portions. However, the testing machine typically is limited to pivot the first and second portions of the case at small angles.

Therefore, there is room for improvement within the art.

BRIEF DESCRIPTION OF THE DRAWINGS

Many aspects of the present cycle life testing machine can be better understood with reference to the following drawings. The components in the drawings are not necessarily drawn to scale, the emphasis instead being placed upon clearly illustrating the principles of the present cycle life testing machine. Moreover, in the drawings, like reference numerals designate corresponding parts throughout the several views.

DETAILED DESCRIPTION

FIGS. 1 through 6 show an exemplary cycle life testing machine 100 for pivotable articles such as pivotable carrying cases for use in carrying and protecting portable electronic device such as mobile phones or tablet personal computers. The pivotable article has a first portion that is hinged to a second portion. Note that hinge is not limited to a mechanical axle-type structure and can cover structures such as bendable strips or any other structure that allows the first portion and the second portion to pivot relative to each other.

Figure 1:
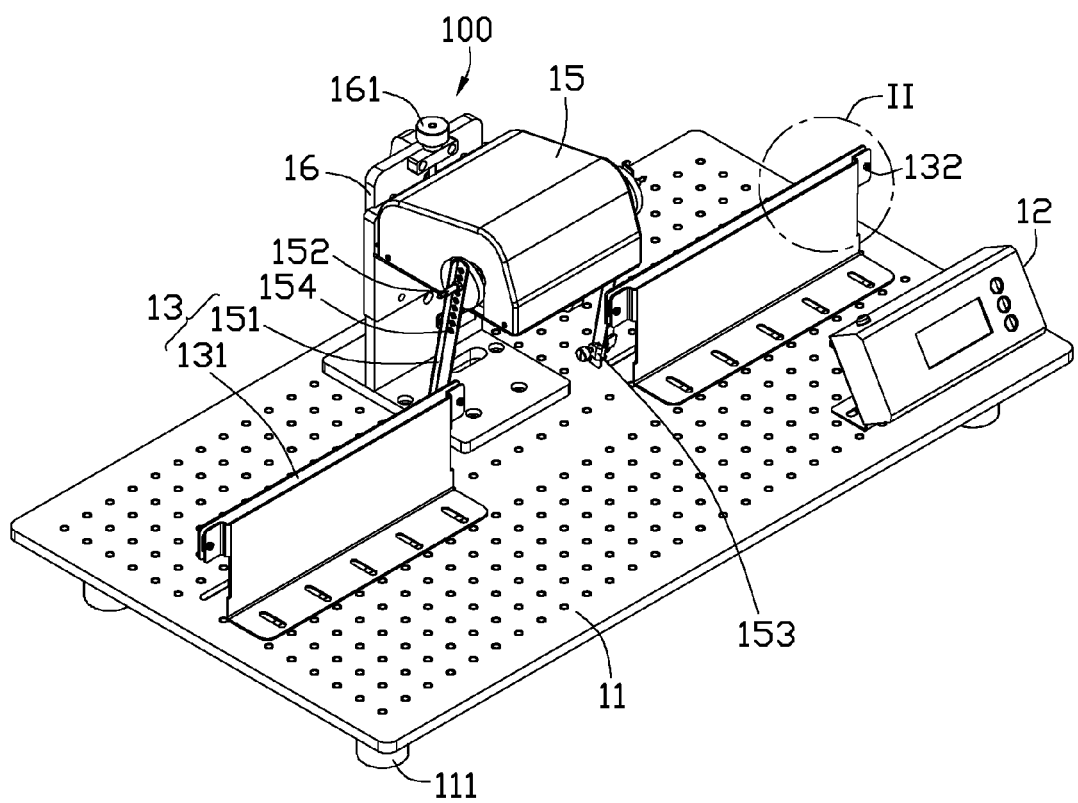
FIG. 1 is an isometric view of a cycle life testing machine according to an exemplary embodiment.
Figure 2:
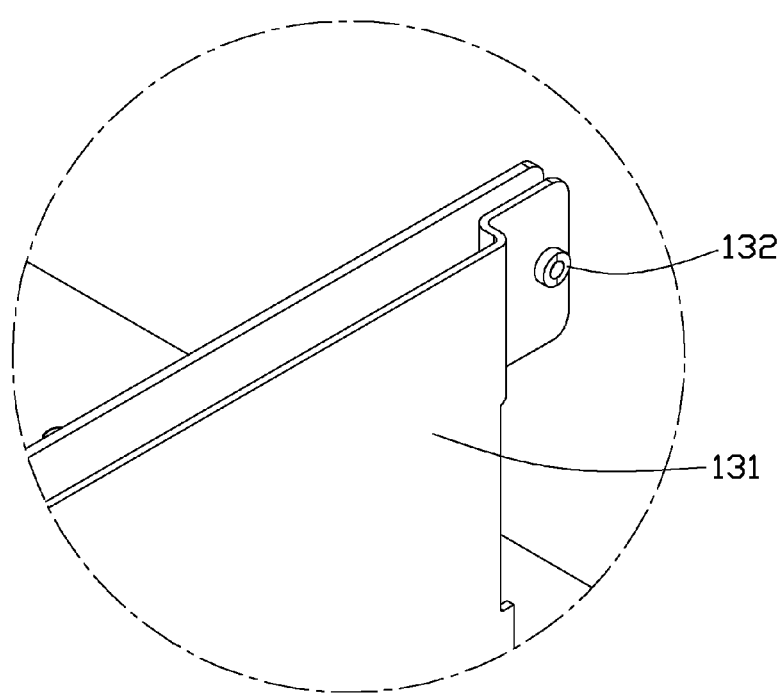
FIG. 2 is an enlarged view of section II shown in FIG. 1.

Referring to FIG. 1, the cycle life testing machine 100 includes a base board 11, a controller 12, two clamping devices 13, an electric cabinet 14, and a cycle device 15. The controller 12 is mounted to the base board 11. The cycle device 15 is mounted and supported by a supporting board 16 above the base board 11. The supporting board 16 is fixed to the base board 11 and extends vertically above the base board 11. The two clamping devices 13 are fixed to the base board 11 at the two sides of the cycle device 15. The electric cabinet 14 is mounted at the bottom surface of the base board 11. The base board 11 may have four supporting feet 111, one at each corner of the bottom surface of base board 11.

Each of the clamping devices 13 includes a clamping assembly 131 and a rod clamping member 153. Each clamping assembly 131 has two metal sheets assembled together (best shown in FIG. 2). One L-shaped metal sheet is fixed to the top of the base board 11, and the other planar metal sheet is releasably attached to the top end of the L-shaped metal sheet by two adjustable clamps 132. The pivotable carrying case 200 can have a first pivotable portion 201 inserted between and clamped by the two metal sheets with clamping of the adjustable clamps 132.

Figure 3:
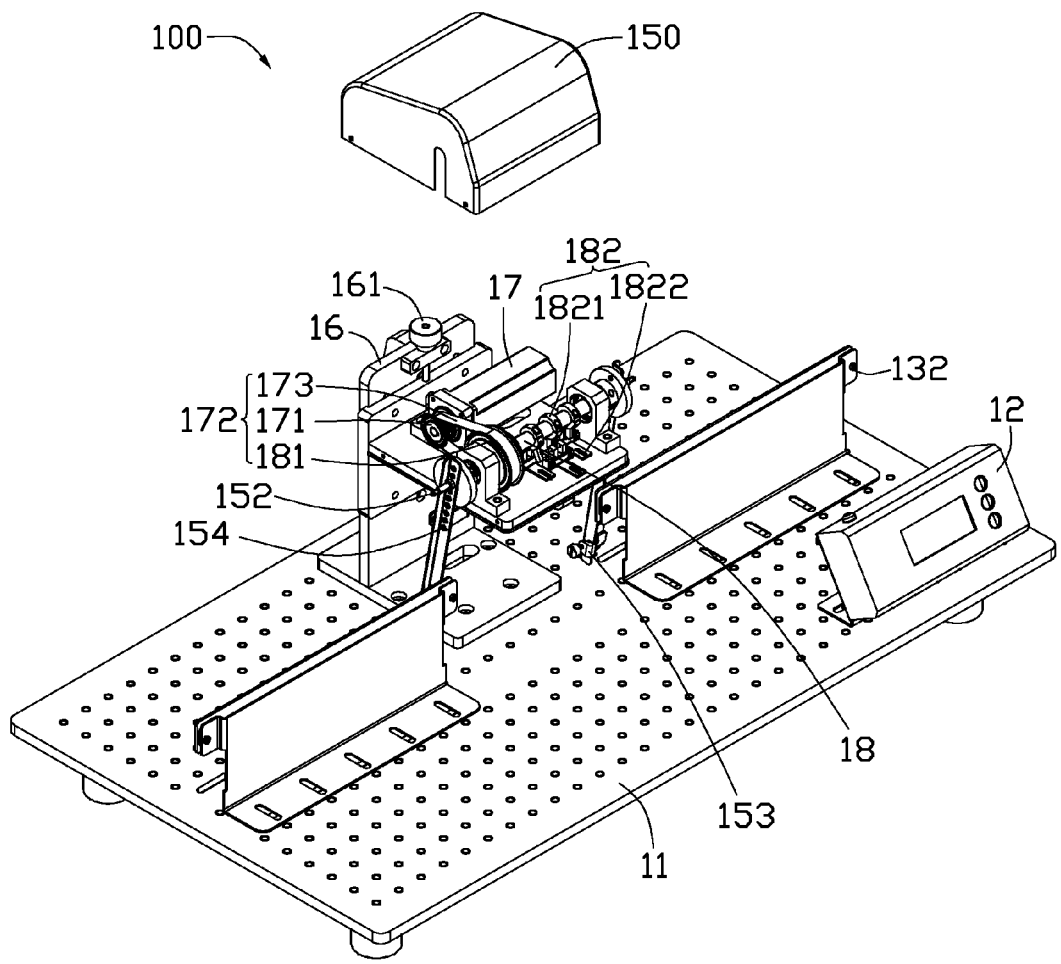
FIG. 3 is isometric view of the cycle life testing machine shown in FIG. 1, with a housing of a cycle device lifted.

FIG. 3 further shows the cycle device 15 including a housing 150, a servo motor 17, a shaft 18, an actuator 172 and two swing rods 151. The servo motor 17 physically connects to the actuator 172. The servo motor 17 drives the transmission movement of the actuator 172. The actuator 172 includes a first wheel 171 directly connecting to the servo motor 17, a second wheel 181 directly connecting to the shaft 18, and a driving belt 173 connecting the first wheel 171 and the second wheel 181.

The shaft 18 extends two shaft pins 152, one from each opposite end, and mounts a limit switch module 182 at the exterior surface. The swing rod 151 defines pin holes 154, each one of which may receive the shaft pin 152 so that swing rod 151 connects with the shaft 18, and the shaft 18 rotates to drive the swings of the swing rod 151. The swing rod 151 further forms the rod clamping member 153 opposite to the pin holes 154 for clamping a second pivotable portion 202 of the pivotable carrying case 200 to the swing rod 151.

The limit switch module 182 includes a first limit switch component 1821 and a second limit switch component 1822 corresponding to the first limit switch component 182. The first limit switch component 1821 is positioned above the second limit switch component 1822. The shaft 18 can rotate along one direction until at an angle where the first limit switch component 1821 is sensed by the second limit switch component 1822 to trigger a stop signal to the controller 12 for stopping the servo motor 17 and further stops rotation of the shaft 18 and the swing of the swing rod 151. At this time, the testing can be stopped for protecting the carrying case 200 from pivoting at too large an angle, and thus protects the carrying case 200 from damage.

Figure 4:
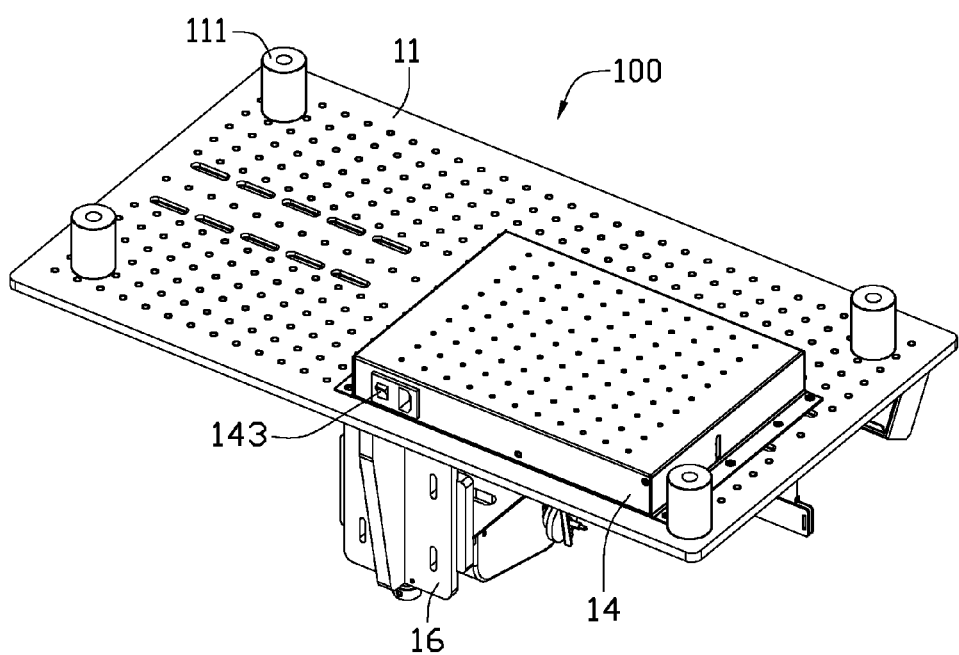
FIG. 4 is an isometric view of the cycle life testing machine shown in FIG. 1, viewed from another angle.
Figure 5:
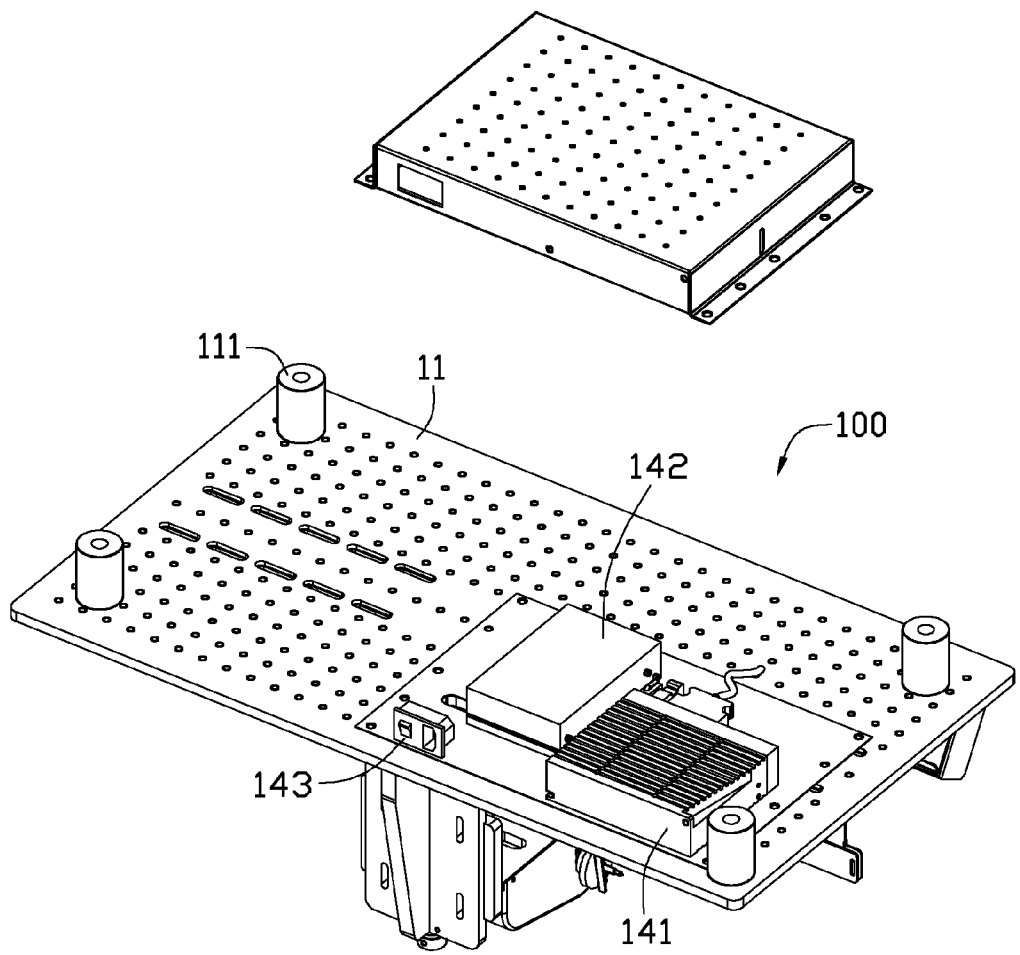
FIG. 5 is an isometric view of the cycle life testing machine shown in FIG. 3, with a housing of a cabinet lifted.

Referring to FIGS. 4 and 5, the electric cabinet 14 includes a switch 143, power supply 141 and a driver 142. The switch 143 can be manipulated to power on or off the cycle life testing machine 100. The power supply 141 is located inside the electric cabinet 14. The driver 142 is a servo drive. The driver 142 electrically connects with the servo motor 17. The controller 12 electronically connects to the electric cabinet 14 and is used for determining and/or displaying technical parameters of the swing rods 151 such as swing angles, swing speeds, and cycle times, and also used for sending signals to the driver 142 to control the servo motor 17.

Figure 6:
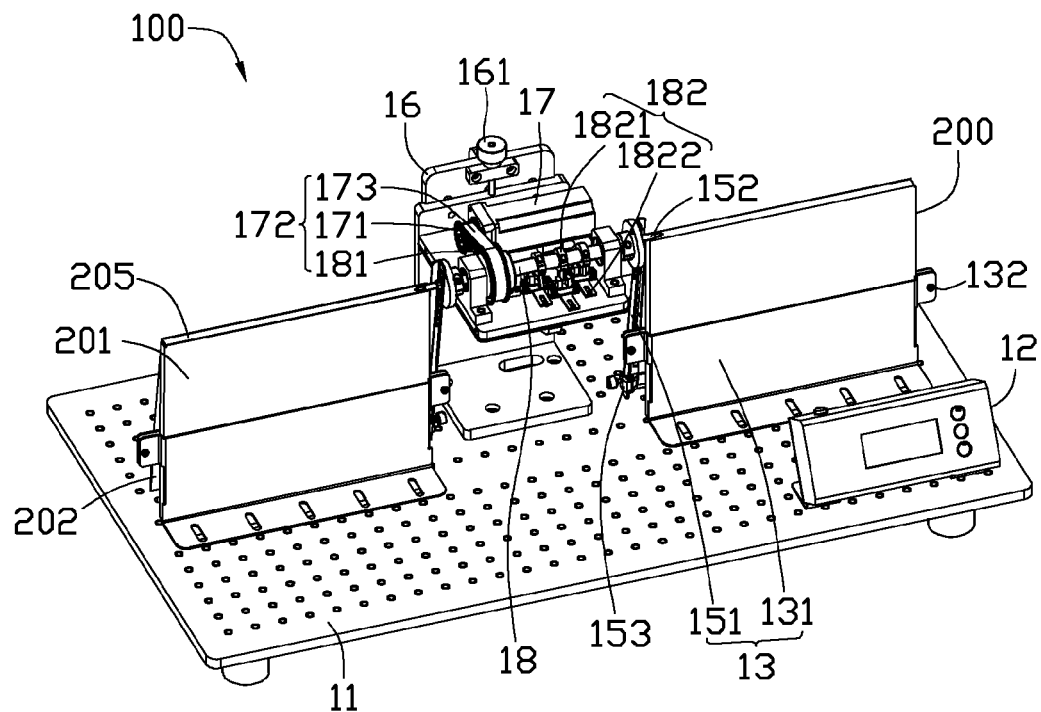
FIG. 6 is an isometric view of the cycle life testing machine shown in FIG. 1, testing a pivotable carrying case.

FIG. 6 shows the carrying case 200 mounted to the machine 100 for cycle life testing. The first pivotable portion 201 of the case 200 is clamped by the clamping assembly 131, the opposite second pivotable portion 202 of the case 200 is clamped by the rod clamping member 153, and the shaft pin 152 is inserted into and positioned below a hinge portion 205 of the case 200 connecting the first and second pivotable portion 201 and 202 to keep the hinge point of the case 200 from moving. The controller 12 sends signals to and controls the driver 142 to trigger working of the servo motor 17. The servo motor 17 rotates the first wheel 171, and the second wheel 181 and the shaft 18 follow to rotate. The swing rods 151 swing by the rotation of the shaft 18 at a speed to an angle specified by the controller 12 along a direction, and then swing along a reversed direction at a speed to an angle specified by the controller 12. The swing process can be cycled at cycle times specified by the controller 12, until the cycle testing is completed. After finishing one cycle of the swing process, the finished cycle times can be displayed by the controller 12.

It is to be understood that even though numerous characteristics and advantages of the present embodiments have been set forth in the foregoing description, together with details of assemblies and functions of various embodiments, the disclosure is illustrative only, and changes may be made in detail, especially in matters of shape, size, and arrangement of parts within the principles of the present disclosure to the full extent indicated by the broad general meaning of the terms in which the appended claims are expressed.

What is claimed is:

1. A cycle life testing machine, comprising:
    a controller for controlling the cycle life testing machine;
    a clamping device comprising a clamping assembly and a rod clamping member, the clamping assembly comprising two metal sheets and an adjustable clamp clamping the two metal sheets for clamping a first pivotable portion of a pivotable article between the two metal sheets; the rod clamping member configured for securing a second pivotable portion of the pivotable article and which is pivotable relative to the first pivotable portion of the pivotable article;
    an electric cabinet including a driver; and
    a cycle device comprising:
        a servo motor;
        an actuator;
        a shaft; and
        a swing rod connected with the shaft;
        wherein, the rod clamping member forms on the swing rod, the controller sends a signal to control the driver to trigger working of the servo motor, the servo motor drives the actuator and the shaft to rotate to swing the swing rod in a cycle procedure specified by the controller.

2. The cycle life testing machine of claim 1, wherein the shaft extends two shaft pins from two opposite ends, the swing rod defines pin holes, the shaft pin can be adjusted to secure each one of the pin holes.

3. The cycle life testing machine of claim 1, wherein the actuator comprises a first wheel directly connecting to the servo motor, a second wheel directly connecting to the shaft, and a driving belt connecting the first wheel and the second wheel.

4. The cycle life testing machine of claim 1, wherein the electric cabinet further comprises a switch and a power supply, the switch can be manipulated to power on or off the cycle life testing machine, the power supply is located inside the electric cabinet.

5. The cycle life testing machine of claim 1, further comprising a limit switch module comprising a first limit switch component and a second limit switch component, the first limit switch component is positioned above the second limit switch component, the shaft can rotate along one direction until at an angle where the first limit switch component is sensed by the second limit switch component to trigger a stop signal to the controller for stopping the servo motor.

6. The cycle life testing machine of claim 1, wherein the controller electronically connects to the electric cabinet and specifies swing angles, swing speeds, and cycle times of the swing rods.

7. The cycle life testing machine of claim 1, further comprising a base board, the base board, the controller, the clamping device, the electric cabinet, and the cycle device are mounted on the base board.

8. A cycle life testing machine, comprising:
    a controller controlling cycle life testing procedure of the cycle life testing machine;
    a clamping device comprising a clamping assembly and a rod clamping member, the clamping assembly comprising two metal sheets and an adjustable clamp clamping the two metal sheets for clamping a first portion of a pivotable article between the two metal sheets; the rod clamping member configured for securing a second pivotable portion of the pivotable article and which is pivotable relative to the first pivotable portion of the pivotable article;
    an electric cabinet including a driver driven by the controller; and
    a cycle device comprising:
        a servo motor;
        an actuator;
        a shaft; and
        a swing rod connected with the shaft;
        wherein, the servo motor works to rotate the shaft and swing the swing rod by transmission of the actuator according to the cycle life testing procedure, so that in a swing process, the swing rod swings at a speed to an angle specified by the controller along a direction, and then in a second swing process, the swing rod swings along a reversed direction at another speed to another angle specified by the controller, and the first and second swing processes are cycled at cycle times specified by the controller.

9. The cycle life testing machine of claim 8, wherein the shaft extends two shaft pins from two opposite ends, the swing rod defines pin holes, the shaft pin can be adjusted to secure each one of the pin holes.

10. The cycle life testing machine of claim 8, wherein the actuator comprises a first wheel directly connecting to the servo motor, a second wheel directly connecting to the shaft, and a driving belt connecting the first wheel and the second wheel.

11. The cycle life testing machine of claim 8, wherein the electric cabinet further comprises a switch and a power supply, the switch can be manipulated to power on or off the cycle life testing machine, the power supply is located inside the electric cabinet.

12. The cycle life testing machine of claim 8, further comprising a limit switch module comprising a first limit switch component and a second limit switch component, the first limit switch component is positioned above the second limit switch component, the shaft can rotate along one direction until at an angle where the first limit switch component is sensed by the second limit switch component to trigger a stop signal to the controller for stopping the servo motor.

13. The cycle life testing machine of claim 8, wherein the controller electronically connects to the electric cabinet and specifies swing angles, swing speeds, and cycle times of the swing rods.

14. The cycle life testing machine of claim 8, further comprising a base board, the base board, the controller, the clamping device, the electric cabinet, and the cycle device are mounted on the base board.

15. A cycle life testing machine for a pivotable article that comprises a first pivotable portion, a second pivotable portion pivotable relative to the first pivotable portion, and a hinge portion connecting the first pivotable portion with the second pivotable portion, the cycle life testing machine comprising:
    a controller for controlling the cycle life testing machine;
    a clamping device comprising a clamping assembly and a rod clamping member, the clamping assembly configured for clamping the first pivotable portion; the rod clamping member configured for securing the second pivotable portion;

an electric cabinet including a driver; and
a cycle device comprising:
- a servo motor;
- an actuator;
- a shaft having a shaft pin extending from one end of the shaft, the shaft pin configured to be inserted into and positioned below the hinge portion of the pivotable article to keep the hinge portion from moving; and
- a swing rod connected with the shaft;
- wherein, the rod clamping member forms on the swing rod, the controller sends a signal to control the driver to trigger working of the servo motor, the servo motor drives the actuator and the shaft to rotate to swing the swing rod in a cycle procedure specified by the controller.

16. The cycle life testing machine of claim 15, wherein the swing rod defines a plurality of pin holes, the shaft pin can be adjusted to secure each one of the pin hole.

17. The cycle life testing machine of claim 15, wherein the clamping assembly comprising two metal sheets and an adjustable clamp clamping the two metal sheets to clamping the first pivotable portion between the two metal sheets.

18. The cycle life testing machine of claim 15, wherein the actuator comprises a first wheel directly connecting to the servo motor, a second wheel directly connecting to the shaft, and a driving belt connecting the first wheel and the second wheel.

19. The cycle life testing machine of claim 15, further comprising a limit switch module comprising a first limit switch component and a second limit switch component, the first limit switch component is positioned above the second limit switch component, the shaft can rotate along one direction until at an angle where the first limit switch component is sensed by the second limit switch component to trigger a stop signal to the controller for stopping the servo motor.

* * * * *